US00PP26239P2

(12) United States Plant Patent
de Groot

(10) Patent No.: US PP26,239 P2
(45) Date of Patent: Dec. 15, 2015

(54) ***HYPERICUM* PLANT NAMED 'RUIHYG224A'**

(50) Latin Name: *Hypericum×inodorum*
Varietal Denomination: Ruihyg224a

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 121 days.

(21) Appl. No.: 13/998,759

(22) Filed: Dec. 3, 2013

(51) Int. Cl.
*A01H 5/00* (2006.01)

(52) U.S. Cl.
USPC ..... Plt./442

(58) Field of Classification Search
USPC ..... Plt./442
CPC ..... A01H 5/02; A01H 5/00
See application file for complete search history.

(56) References Cited

PUBLICATIONS

UPOVPROM Plant Variety Database as per CA PBR 12-7753, Oct. 31, 2012, 1 page.*

* cited by examiner

*Primary Examiner* — Kent L Bell
(74) *Attorney, Agent, or Firm* — Penny J. Aguirre

(57) ABSTRACT

A new cultivar of *Hypericum×inodorum*, 'Ruihyg224a', that is characterized by its compact plant habit suitable for container growing, its medium sized berries that are light pink in color and oval in shape, and its small sized light green sepals.

2 Drawing Sheets

Botanical classification: *Hypericum×inodorum.*
Variety denomination: 'Ruihyg224a'.

BACKGROUND OF THE INVENTION

The present invention relates to a new and distinct cultivar of *Hypericum×inodorum* and will be referred to hereafter by its cultivar name, 'Ruihyg224a'. 'Ruihyg224a' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with unique berries and improved resistance to *Melampsora hypericorum.*

The new cultivar arose from a cross made by the Inventor in Hazerswoude, The Netherlands in April 2006 between an unnamed plant from the Inventor's breeding program, designated 'Hp-04-0105-005' as the female parent and 'Annelies Hypearl' (not patented) as the male parent. The Inventor selected 'Ruihyg224a' as a single unique plant amongst the seedlings that resulted from the above cross in autumn of 2007.

Asexual propagation of the new cultivar was first accomplished by the Inventor by vegetative stem cuttings in 2009 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyg224a' as a unique cultivar of *Hypericum.*

1. 'Ruihyg224a' exhibits a compact plant habit suitable for container growing.
2. 'Ruihyg224a' exhibits medium sized berries that are light pink in color and oval in shape.
3. 'Ruihyg224a' exhibits small sized light green sepals.

The female parent of 'Ruihyg224a', 'Hp-04-0105-005', differs from 'Ruihyg224a' in having berries that are light red in color. The male parent of 'Ruihyg224a', 'Annelies Hypearyl', differs from 'Ruihyg224a' in having berries that are green in color. 'Ruihyg224a' can be most closely compared to the cultivar 'Coral Hypearl' (not patented). 'Coral Hypearl' differs from 'Ruihyg224a' in having berries that are pinkish red in color and pyramidal in shape and in having sepals that are smaller in size.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse in Lelystad, The Netherlands.

The photograph in FIG. 1 provides a side view of 'Ruihyg224a' in bloom.

Figure 1:
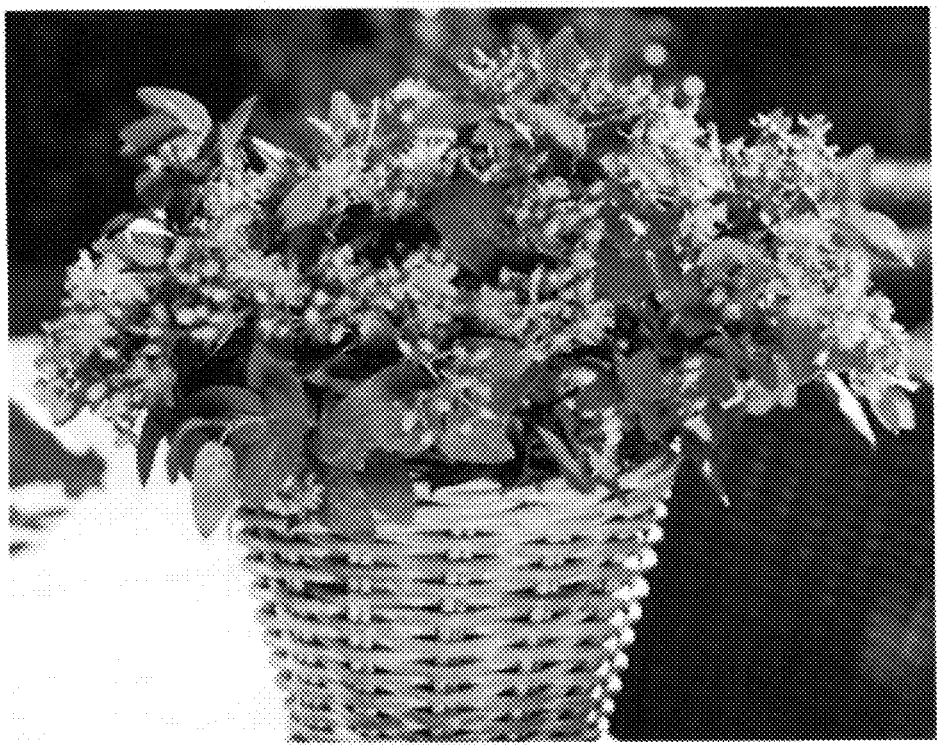
Figure 2:
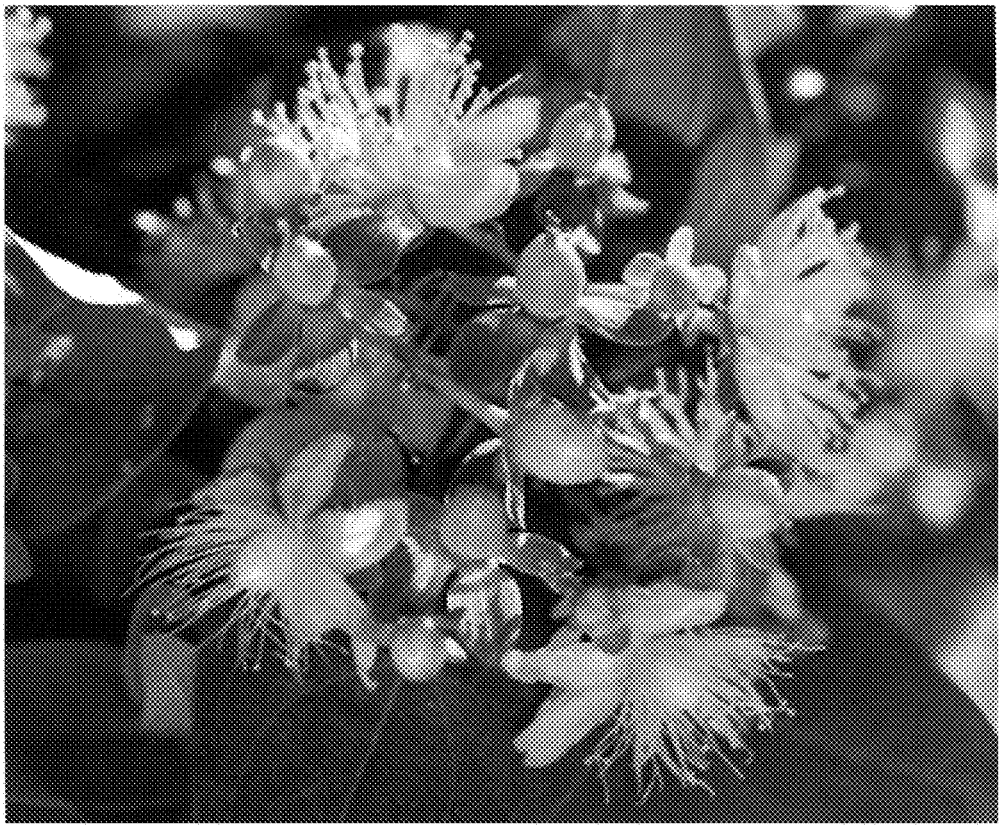

The photograph in FIG. 2 provides a close-up view of the flowers and berries of 'Ruihyg224a'.

The colors in the photographs are as close as possible with the digital photography techniques available, the color values cited in the detailed botanical description accurately describe the colors of the new *Hypericum.*

DETAILED BOTANICAL DESCRIPTION

The following is a detailed description of two year-old plants of the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July to September in The Netherlands.

*Plant type*.—Semi-evergreen shrub.

*Plant habit*.—Compact with suitability for container growing.

*Height and spread*.—Reaches an average of 40 cm in height and spread.

*Cold hardiness*.—Observed to be hardy to at least −10° C.

*Diseases*.—Has shown tolerance to *Melampsora hypericorum*.

*Root description*.—Fibrous and fine.

*Propagation*.—Vegetative stem cuttings.

*Growth rate*.—Moderate, typical for cultivars of *Hypericum×inodorum*.

Stem description:

*Shape*.—Round.

*Stem color*.—New growth, 144C, maturing branches become 165A as they become woody.

*Stem size*.—Main stems; average of 35 cm in length and 1 cm in diameter, lateral branches; an average of 30 cm in length and 5 mm in width.

*Stem surface*.—Glabrous.

*Internode length*.—Average of 7 mm.

*Branching*.—Freely branched with lateral branches upright to an average of a 45° angle from vertical.

Foliage description:

*Leaf shape*.—Elliptic.

*Leaf division*.—Simple.

*Leaf base*.—Cuneate to rounded.

*Leaf apex*.—Broadly acute.

*Leaf fragrance*.—None.

*Leaf venation*.—Pinnate, slightly conspicuous, 144D on upper surface, 138B to 138C on lower surface.

*Leaf margins*.—Entire.

*Leaf arrangement*.—Opposite, aspect is horizontal.

*Leaf attachment*.—Sessile.

*Leaf substance*.—Slightly thick on mature leaves.

*Leaf surface*.—Glabrous on upper and lower surface with lower surface appearing slightly glaucous.

*Leaf size*.—Up to about 3.5 cm in length, up to about 1.9 cm in width.

*Leaf color*.—Newly expanded leaves; upper surface a color between 137A and 137B lower surface 138B, mature leaves; upper surface 147A, lower surface 191A.

Inflorescence description:

*Inflorescence type*.—Solitary flowers from terminal of lateral branches.

*Flower buds*.—Conical in shape with bluntly acute apex, up to 9 mm in length and 8 mm in width prior to opening, calyx portion is slightly wrapped around petals and 143A in color, petal portion is 22A in color.

*Flower fragrance*.—Light citrus fragrance.

*Flower quantity*.—Average of 9 lateral branches.

*Flower type*.—Complete, rotate with reflexed petals and prominent stamens and ovary.

*Flower aspect*.—Upward facing.

*Flower lastingness*.—About 5 days.

*Flower size*.—Average of 1.5 cm in diameter and 1.8 cm in depth.

*Petals*.—5, oblong in shape, un-fused, curved inward, both surfaces glabrous and satiny, entire margin, cuneate base, acute apex, 7 mm in length and 4 mm in width, color is 20A (opening and mature, lower and upper surface).

*Calyx*.—Reflexed, unfused sepals, about 2 cm in diameter and 3 mm in depth.

*Sepals*.—5, lanceolate in shape, 138A in color on upper surface and 138B in color on lower surface, glabrous on upper and lower surface, 7 mm length and 6 mm in width, entire margin, round-truncate base, acute-attenuate apex.

*Peduncles*.—Up to 1 cm in length, 1 mm in width, 145A in color, glabrous surface.

*Pedicels*.—About 1 cm in length, 1 mm in width, 145A in color, glabrous surface.

Reproductive organs:

*Gynoecium*.—Compound pistil about 1 cm in length and 0.5 cm in width, styles; 3, 187A in color and about 8 mm in length and 0.5 mm in width, stigmas; 3, 150A in color about 0.5 mm in diameter, ovary is superior and 150A, becoming blushed with 38B in color, about 4 mm in length and 3 mm in width.

*Androecium*.—Numerous stamens (about 80, arranged in 5 tufts), spreading outward from base of ovary extending about 1.5 cm in diameter, filaments are 11A in color, about 6 mm in length and 0.4 mm in width, anthers are 17B in color, dorsifixed, about 1 mm in length and 0.5 in width, pollen is moderate and 17C in color.

*Fruit*.—Fruit, rotund in shape, glabrous and satiny surface, and average of 6 mm in length and width, 37A in color when mature.

It is claimed:

1. A new and distinct cultivar of *Hypericum* plant named 'Ruihyg224a' as herein illustrated and described.

* * * * *